United States Patent [19]

Frisbie et al.

[11] Patent Number: 4,619,263
[45] Date of Patent: Oct. 28, 1986

[54] ADJUSTABLE ROTATION LIMITER DEVICE FOR STEERABLE DILATATION CATHETERS

[75] Inventors: Jeffrey S. Frisbie, San Jose; Wilfred J. Samson, Saratoga, both of Calif.

[73] Assignee: Advanced Cardiovascular Systems, Inc., Mountain View, Calif.

[21] Appl. No.: 732,641

[22] Filed: May 10, 1985

Related U.S. Application Data

[63] Continuation-in-part of Ser. No. 615,139, May 30, 1984, abandoned.

[51] Int. Cl.⁴ .............................................. A61M 29/02
[52] U.S. Cl. ..................................... 128/344; 128/657; 128/772; 604/96
[58] Field of Search ............... 128/344, 343, 772, 657; 604/95–102, 164, 165, 171

[56] References Cited

U.S. PATENT DOCUMENTS

| | | | |
|---|---|---|---|
| 3,503,385 | 3/1970 | Stevens | 128/657 |
| 3,552,384 | 1/1971 | Pierie et al. | 128/657 |
| 4,292,974 | 10/1981 | Fogarty et al. | 604/98 |
| 4,332,254 | 6/1982 | Lundquist | 128/344 |
| 4,338,942 | 7/1982 | Fogarty | 604/99 |
| 4,403,612 | 9/1983 | Fogarty | 128/344 |
| 4,422,447 | 12/1983 | Schiff | 128/344 |

Primary Examiner—Robert Peshock
Assistant Examiner—Cary E. Stone
Attorney, Agent, or Firm—Flehr, Hohbach, Test, Albritton & Herbert

[57] ABSTRACT

Adjustable rotation limiter device for use with a steerable balloon type dilatation catheter of the type having a flexible core wire extending therethrough and an adapter adapted to be secured to the proximal extremity of a dilatation catheter. The adapter has at least a first arm with a fitting thereon. A sealing is disposed within the fitting. A thumb screw having a first knob carrying a threaded axially extending member is threaded into the fitting and is adapted to engage the seal whereby when a core wire extends through the fitting, the seal, and the thumb screw, the rotation of the thumb screw in one direction will cause sealing engagement between the seal and the core wire. A torque knob having a second knob carrying an axially extending member is threaded into said thumb screw. A rotation limiter is carried by one of the knobs and has a portion thereof extending over the other of the knobs which serves to limit the rotational movement of the second knob with respect to the first knob.

12 Claims, 6 Drawing Figures

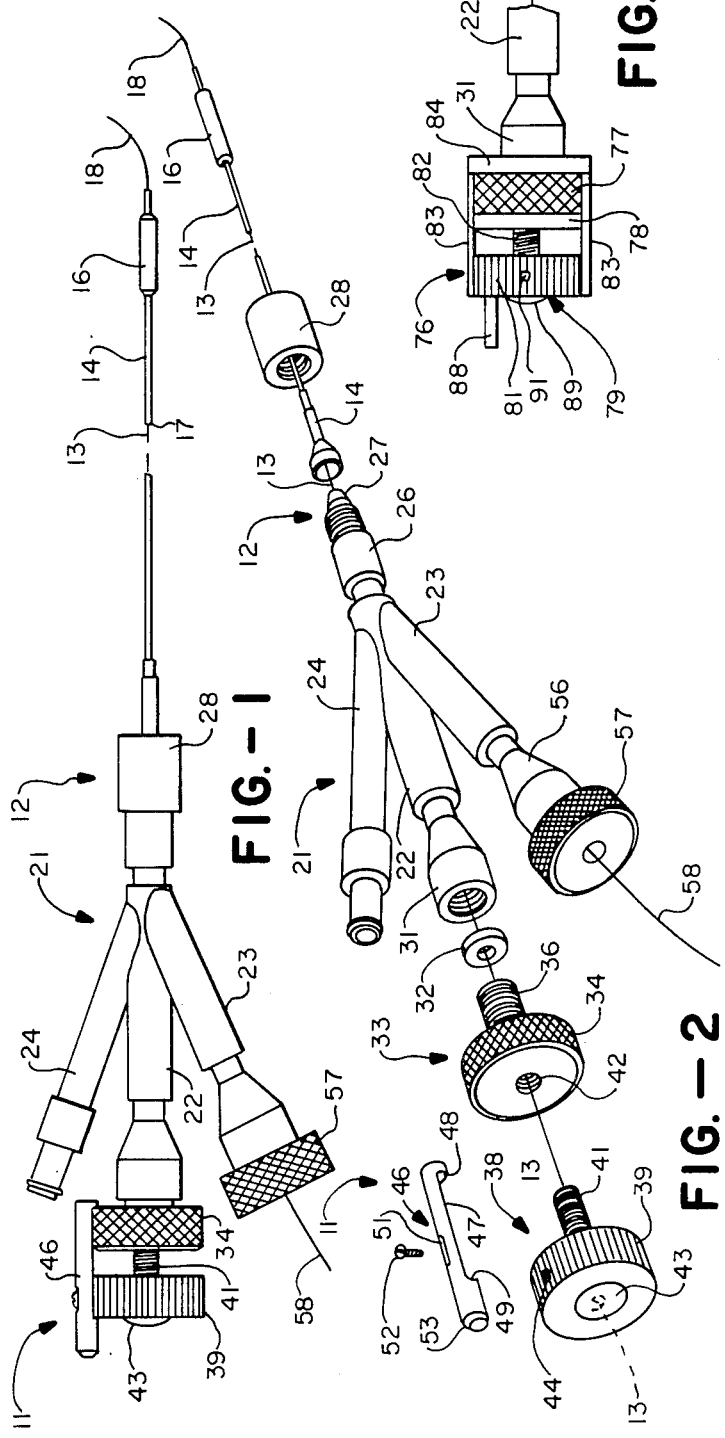
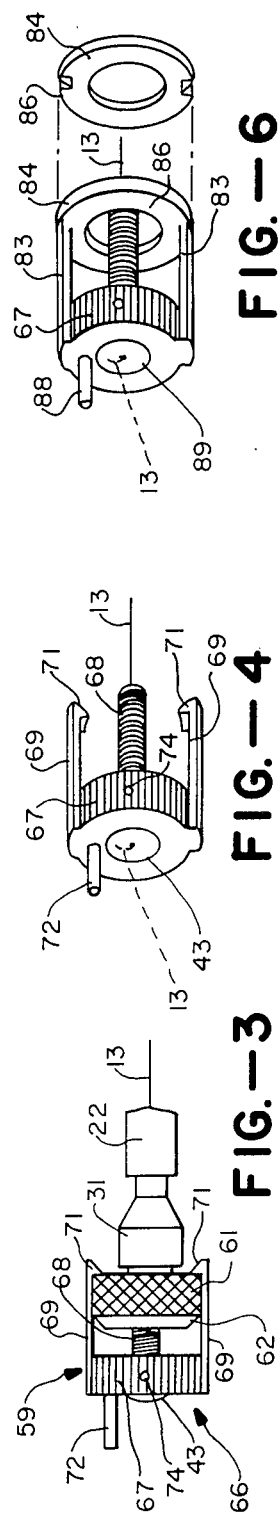

ADJUSTABLE ROTATION LIMITER DEVICE FOR STEERABLE DILATATION CATHETERS

This application is a continuation-in-part of application Ser. No. 615,139 filed on May 30, 1984 now abandoned.

This invention relates to adjustable rotation limiter devices for steerable dilatation catheters of the low-profile balloon type and more particularly to such adjustable rotation limiter devices which are factory adjustable.

In co-pending application Ser. No. 615,141 filed May 30, 1984 now U.S. Pat. No. 4,573,470 there is disclosed a low-profile steerable intraoperative balloon dilatation catheter which has no rotation limiting capability. In co-pending application Ser. No. 615,118 filed May 30, 1984, there is disclosed a low-profile steerable dilatation catheter which is provided with rotation limiting means which utilizes rotation limiting discs with pins mounted therein. By changing the number of discs, the number of revolutions of the torque knob can be controlled. It has been found that there is a need for a simpler rotation limiting device and also that there is a need for providing one which is more readily adjustable.

In general, it is an object of the present invention to provide an adjustable rotation limiter device for steerable low-profile balloon dilatation catheters.

Another object of the invention is to provide a device of the above character which can be readily adjusted to adjust the number of revolutions of rotation which can be accomplished.

Another object of the invention is to provide a device of the above character in which the number of revolutions of rotation is positively controlled.

Another object of the invention is to provide a device of the above character which is relatively simple in construction and can be readily manufactured.

Additional objects and features of the invention will appear from the following description in which the preferred embodiments are set forth in detail in conjunction with the accompanying drawing.

FIG. 1 is a side elevational view of an adjustable rotation limiter device incorporating the present invention and being mounted upon a steerable balloon dilatation catheter.

FIG. 2 is an isometric exploded view of the adjustable rotation limiter device shown in FIG. 1.

FIG. 3 is a side elevational view of another embodiment of an adjustable rotation limiter device incorporating the present invention.

FIG. 4 is an isometric view of the torque knob used in the rotation limiter shown in FIG. 3.

FIG. 5 is a side elevational view of still another embodiment of an adjustable rotational limiter device incorporating the present invention.

FIG. 6 is an isometric view of the torque knob utilized in the rotation limiter device shown in FIG. 5.

In general, the adjustable rotation limiter device of the present invention is for use with steerable low-profile balloon dilatation catheters of the type which have a flexible core wire extending therethrough. An adapter is adapted to be secured to the proximal extremity of the dilatation catheter and has at least first and second arms. A fitting is carried by the first arm. Sealing means is disposed in the fitting. A first knob having a threaded axially extending member is threaded into the fitting and is adapted to engage the sealing means whereby when a core wire extends through the fitting, the sealing means and the first knob having the threaded member thereon, rotation of the first knob in one direction will cause the sealing means to form a sealing engagement with the core wire. A second knob which has a threaded axially extending member is threaded into the member carried by the first knob. Limit means is carried by one of the first and second knobs and has a portion thereof extending over the other of said knobs and serves to limit the rotational movement of the second knob with respect to the first knob. Means is provided for adjustably positioning the limit member carried by said one knob axially of the one knob whereby the number of revolutions of the second knob with respect to the first knob may be adjusted.

More particularly as shown in FIGS. 1 and 2 of the drawings, the rotation limiter device 11 is shown as a part of a low-profile steerable dilatation catheter 12. The low-profile steerable dilatation catheter 12 is the type described in co-pending application Ser. No. 615,118 filed May 3, 1984. As disclosed therein, it consists of a flexible core wire 13 formed of a suitable material such as stainless steel. It typically is formed of a length of 150 centimeters for a conventional catheter or approximately 40 centimeters for an intraoperative catheter. The core wire 13 is preferably circular in cross-section and has a diameter which is greater than 0.013 of an inch. As explained in said co-pending application Ser. No. 615,118 filed May 30, 1984, the distal extremity of the core wire can be necked down at the distal extremity to provide greater flexibility at the distal extremity of the core wire.

A flexible tubular member 14 formed of a suitable plastic material extends over the length of the core wire 13. A balloon 16 is carried by the distal extremity of the tubular member 14 and preferably is formed integral with the tubular member 14. The tubular member 14 provides an annular flow passage or lumen 17 in conjunction with the core wire 13 which extends the length of the core wire from the proximal end to the distal end of the tubular member 14 to establish communication with the balloon 16. The distal extremity of the balloon 16 is bonded to the distal extremity of the core wire 13 to form a liquidtight seal therebetween. A flexible tip 18 is formed on the distal extremity of the core wire 13.

A triple arm adapter 21 is secured to the proximal extremity of the tubular member 14. It is provided with a first or central arm 22 and second and third side arms 23 and 24. The adapter 21 is provided with a fitting 26 which has a threaded exterior with a conical distal extremity 27 over which the proximal extremity of the tubular member 14 is adapted to fit. An interiorly threaded cylindrical member 28 is provided for retaining the proximal extremity of the tubular member 14 on the conical portion 27 and is threaded onto the fitting 26.

The central arm 22 carries an interiorly threaded fitting 31 which is generally conical in shape and is adapted to receive sealing means in the form of an O-ring 32. A thumb screw 33 is provided for engaging the O-ring 32 and clamping it into sealing engagement with the core wire 13 which extends through the central arm 22 through the fitting 31 through the O-ring 32 and through the thumb screw 33.

The thumb screw 33 consists of a knurled knob 34 and carries an exteriorly threaded axially extending extension or member 36 which is adapted to be threaded into the fitting 31 and engage the O-ring 32. A torque knob 38 is provided for imparting rotational movement to the core wire 13 and consists of a knurled knob 39 which has an exteriorally threaded axially extending extension or member 41 carried thereby which is adapted to be threaded into an interiorly threaded bore 42 provided in the thumb screw 33. As shown, the core wire 13 extends through the torque knob 38 and is secured therein in a suitable manner such as by the use of plastic 43 and a set screw 44 threaded into the knob and engaging the core wire 13 so that the core wire 13 will be rotated by the torque knob.

The rotation limiter device 11 in addition to including the torque knob 38 includes a stop member 46 which is generally in the form of an elongate cylinder. It is provided with an elongate cutout 47 extending longitudinally of the stop member. The cutout 47 provides spaced apart parallel lips 48 and 49. The stop member 46 is also provided with an elongate slot 51 which opens through the cutout 47. The slot 51 is adapted to receive a screw 52. The screw 52 extends through the slot and is adapted to secure the stop member 46 to one of the knobs carried either by the thumb screw 33 or by the torque knob 38. As shown in the drawings, the stop member 46 is secured to the knob 39 in such a manner that the lips 48 and 49 underlie the knob 34 and overlie the knob 39 for a purpose hereinafter described. The stop member is provided with a conical upper end 53 which is readily adapted to be engaged by a finger of the human hand.

The side arm 23 also carries a fitting 56 similar to the fitting 31 carried by the central arm 22 and is provided with an O-ring (not shown) which is adapted to be engaged by a thumb screw 57. A bleed or vent wire 58 extends through the thumb screw 57 and through the arm 23 into the lumen provided by the tubular member 14 and into the distal extremity of the balloon 16. The other arm 24 is adapted to receive a syringe or other suitable inflating device for introducing a saline solution or radiocontrast liquid into the lumen leading to the balloon 16 to inflate the balloon and to cause inflation of the balloon 16 and to cause any air therein to be expelled through the bleed wire 58. Operation of the adjustable rotation limiter device may now be briefly described as follows. The use of steerable low profile dilatation balloon catheters is well known to those skilled in the art and will not be described in detail. The use of the rotation limiter device, however, in conjunction with the use of such a dilatation catheter will now be described. Let it be assumed that when the dilatation catheter is being manufactured that it is desirable to limit the revolution of the torque knob to a certain number of revolutions as, for example, two. Let it be assumed that each revolution of the torque knob causes axial movement of the torque knob 38 with respect to the thumb screw 33 by an appropriate distance as, for example, 0.020 inches. Thus it can be seen by adjusting the gap between the lip 48 and the lower extremity of the thumb screw 34 that the number of revolutions which the torque knob 38 can be rotated before the lip 48 engages the lower extremity of the thumb screw 33 and prevents further rotation can be readily adjusted. Thus as soon as the desired gap between the lip 48 and the lower extremity of the thumb screw 33 has been ascertained, the stop member 46 can be fixed in position on the knob 39 by tightening the screw 52. If desired, the screw 52 can be provided with special means as, for example, a Phillips head or an Allen head to discourage tampering with the positioning of the stop member 46 away from the factory. By providing a cutout 47 of appropriate length it can be seen that various spacings can be provided between the lip 48 and the lower extremity of the knob 34 of the thumb screw 33. For example, by providing a gap of 0.060 rather than 0.020, the number of revolutions can be increased from 1 to 3.

It also should be appreciated that rather than mounting the stop member 46 on the knob 39, the stop member alternatively can be mounted on the knob 34 in which case the spacing between the lip 49 and the upper surface of the knob 39 would control the number of revolutions for the torque knob 38.

Another embodiment of a rotation limiter device is a device 59 incorporating the present invention shown in FIGS. 3 and 4. As shown therein, it consists of a thumb screw 61 which is threaded into the fitting 31. The thumb screw 61 is similar to the thumb screw 33 hereinbefore described with the exception that it is provided with a chamfer 62 for the purpose hereinafter described. The rotation limiter 59 includes a torque knob 66. The torque knob 66 consists of a knob 67 which carries an externally threaded axially extending extension member 68. The torque knob 66 can be formed of a suitable material such as plastic and is provided with first and second diametrically opposed legs or arms 69 which extend in a direction parallel to the member 68. The distal extremities of the arms 69 are provided with inwardly extending abutments or lips 71 which are formed integral therewith and which are spaced a predetermined distance from the innermost surface of the knob 67. An upstanding protrusion 72 is formed on the knob 67 and is offset to one side thereof and extends outwardly from the outer extremity of the knob 67. The protrusion 72 is adapted to be engaged by a finger of a hand. The guide wire 13 hereinbefore described extends through the torque knob 66 and is secured thereto by an epoxy 43 as well as by a set screw 74.

Operation of this embodiment of the rotation limiter device 59 is similar to that hereinbefore described in conjunction with FIGS. 1 and 2. In assembling the rotation limiter device, the torque knob 66 has its member 68 threaded into the thumb screw 61 in such a manner so that the lowermost curved extremities of the abutments or lips 71 engage the chamfer 62 on the thumb screw 61. The chamfer 62 urges the lower extremities of the arms 69 outwardly as continued rotation of the torque knob 66 moves the legs or arms 69 downwardly until the abutments or lips 71 clear the side margins of the thumb screw and thereafter snap over the lower extremities of the thumb screw 61.

As soon as this occurs, it can be seen that the torque knob 66 can continue to be rotated until the lower surface of the knob 67 engages the upper surface of the thumb screw 61. Also, it can be seen that the amount of rotation of the torque knob 67 is limited by the arms 69, with the number of rotations of the torque knob 66 being controlled by the full length of the arms 69. As soon as the lips or abutments 71 engage the lower surface of the thumb screw 61, further rotation will be prevented.

It can be seen that by providing torque knobs 66 with arms 69 of variable lengths, that rotation of a torque knob 66 can be limited to a predetermined amount as, for example, one turn, two turns, or three turns, as the case may be. The rotation limiter device 59 in addition to being relatively simple prevents canting of the torque knob 66 because arms or legs 69 are provided on diametrically opposite sides of the threaded arm member 68. In addition, the torque knob 66 can be readily rotated by a finger engaging the cylindrical protrusion 72.

Thus it can be seen that by controlling the length of the slot 51 and the overall spacing between lips 48 and 49 in the embodiment shown in FIGS. 1 and 2 or by providing arms 69 of various lengths in the embodiment shown in FIGS. 3 and 4, the number of possible revolutions can be readily selected. This makes it possible to provide a rotation limiter device which can be utilized with dilatation catheters of various lengths and thereby preventing over rotation of the core wire and undue distortion of the balloon. It also is apparent that there has been provided a relatively simple rotation limiter device which can be readily manufactured which is provided with a minimum number of parts.

Still another embodiment of a rotation limiter device is a device 76 shown in FIGS. 5 and 6 incorporating the present invention. As shown therein, the device 76 consists of a thumb screw 77 which is threaded into the fitting 31. The thumb screw 77 is similar to the thumb screw 61 hereinbefore described with the exception that it is not provided with a chamfer. Thus the thumb screw 77 is provided with a cylindrical unknurled portion 78. The rotation limiter device 76 also includes a torque knob 79. The torque knob 79 includes a cylindrical member 81 in the form of a knob which carries an external axially extending extension member 82. The torque knob 79 is provided with first and second diametrically opposed legs or arms 83 which extend in a direction parallel to the extension member 82. Means is carried by the distal extremities of the legs or arms 83 to stiffen the legs or arms and to prevent the legs or arms 83 from being cammed outwardly and consists of a ring 84 which has its outer circumference bonded to the distal extremities of the leg 83 by suitable means such as an epoxy. The ring 84 is provided with upper and lower annular surfaces 86. The upper surface 86 is adapted to engage and seat against the lower surface of the thumb screw 77 as hereinafter described. A protrusion 88 is carried by the torque knob 79 and is adapted to be engaged by the finger of a hand to facilitate rotation of the torque knob 79. The guide wire 13 hereinbefore described extends through the torque knob 79 and is secured thereto by a body 89 of a suitable epoxy as well as by a set screw 91.

In manufacture of the rotation limiter device 76, the assembly is the same as hereinbefore described with respect to the previous embodiments except that the ring 84 is bonded to the distal extremities of the legs 83 after the legs 83 have been passed over the torque knob 79. As soon as this has been accomplished, the circumferential portions of the ring 84 can be bonded to the distal extremities of the legs 83 by suitable means such as an epoxy.

Operation of this embodiment of the rotation limiter device is similar to that hereinbefore described in conjunction with the embodiment shown in FIGS. 3 and 4. The length of the legs 83 as well as the pitch of the threads on the extension member 82 have been chosen so that the desired amount of rotation can be obtained, as for example, three rotations, through 360° for each rotation.

With the arrangement shown it can be seen that the torque knob 79 can be rotated in counterclockwise direction so that the torque knob 79 moves outwardly with respect to the thumb screw 77. This can continue until the top surface 86 of the annular ring 84 comes into engagement with the lower surface of the thumb screw 77 inhibiting further rotation. Typically the length of the legs and the relationship with the threads on the extension member 82 can be selected so that a predetermined number of turns as, for example, a maximum of three turns are permitted. This helps to ensure that there will not be over rotation of the balloon carried by the catheter. The use of the annular ring 84 is particularly advantageous in that it prohibits any inadvertent possible snapping outwardly of the legs 83 and thus provides assurance that the rotation of the guide wire 18 cannot exceed a total of three revolutions. It should be appreciated that if desired, the legs or arms 83 can be made shorter or longer with respect to the threads on the extension member 82 to provide the desired number of revolutions. This makes it possible to precisely control the rotation so that the balloon carried by the end of the catheter will not be unduly twisted.

It is apparent from the foregoing that there has been provided a rotation limiting device in various types of embodiments serving to prevent undue rotation of the balloon carried by the catheter. The rotation limiting devices are relatively simple in construction and can be readily and economically manufactured.

What is claimed is:

1. An adjustable rotation limiter device for use with a steerable balloon type dilatation catheter of the type having a flexible core wire extending therethrough, an adapter adapted to be secured to the proximal extremity of a dilatation catheter, the adapter having at least a first arm, a fitting on the first arm, sealing means disposed within the fitting, a thumb screw having a first knob carrying a threaded axially extending member threaded into the fitting and being adapted to engage the sealing means to establish a sealing engagement between the sealing means and the core wire, a torque knob having a second knob carrying an axially extending member threaded into said thumb screw and limit means carried by one of said knobs and having a portion thereof extending over the other of said first and second knobs and serving to limit the rotational movement of the second knob with respect to the first knob.

2. A device as in claim 1 wherein said limit means includes a limit member and means for adjustably positioning said limit member axially of said one knob whereby the number of revolutions of said second knob with respect to said first knob may be adjusted.

3. A device as in claim 2 wherein said limit member is provided with a cutout forming first and second spaced apart generally parallel lips adapted to engage surfaces of said first and second knobs.

4. A device as in claim 3 wherein said limit member is provided with an elongate slot and screw means extending through said slot and securing said limit member to said first knob.

5. A device as in claim 4 wherein said screw means is provided with means inhibiting adjustment of the position of the limit member outside of the factory.

6. A device as in claim 1 wherein said limit means includes a limit member formed integral with one of said knobs.

7. A device as in claim 6 wherein said limit means includes first and second limit members formed integral with one of said knobs, said limit members having inwardly extending lips adapted to engage the other of said knobs.

8. A device as in claim 7 wherein the other of said knobs is provided with a chamfer engagable by said arms carried by said one knob.

9. A device as in claim 1 wherein said limit means includes first and second limit members carried by one of said knobs and an annular ring secured to the distal extremities of the limit members, said annular member being adapted to engage the underside of the other of said knobs to inhibit further rotation of one knob with respect to the other.

10. An adjustable rotation limiter for use with a steerable balloon-type dilatation catheter of the type having a flexible core wire extending therethrough, an adapter adapted to be secured to the proximal extremity of the dilatation catheter, the adapter having a first arm, the core wire extending therethrough and means carried by the first arm for forming a liquid-tight seal between the arm and core wire, first and second knobs, means for securing one of the knobs to the catheter and means for securing the core wire to the other of the knobs, means interconnecting the first and second knobs whereby one knob can be rotated with respect to the other and rotation limiting means carried by said first and second knobs, said rotation limiting means including means carried by first of said knobs and underlying the other of said knobs to prevent rotation of said first knob with respect to the second knob more than a predetermined number of revolutions.

11. A rotation limiter device as in claim 10 wherein said rotating limiting means includes a pair of diametrically disposed arms carried by the first knob and an annular member underlying the second knob and secured to the distal extremities of the arms.

12. A rotation limiter device as in claim 10 wherein said means permitting relative rotation between the first and second knobs includes an externally threaded extension member carried by the first knob and threaded into the second knob.

* * * * *